United States Patent
Graves

(10) Patent No.: US 6,546,071 B2
(45) Date of Patent: Apr. 8, 2003

(54) ANALYSIS OF SAMPLES

(75) Inventor: Mark Graves, Sutton Coldfield (GB)

(73) Assignee: Spectral Fusion Technologies Limited, Coleshill (GB)

(*) Notice: Subject to any disclaimer, the term of this patent is extended or adjusted under 35 U.S.C. 154(b) by 0 days.

(21) Appl. No.: 09/863,344

(22) Filed: May 23, 2001

(65) Prior Publication Data

US 2002/0012419 A1 Jan. 31, 2002

(30) Foreign Application Priority Data

May 25, 2000 (GB) .............................................. 0012629
Jul. 12, 2000 (GB) .............................................. 0017010

(51) Int. Cl.$^7$ .............................................. G01N 23/06
(52) U.S. Cl. .............................. 378/53; 378/45; 378/86
(58) Field of Search ........................ 378/44–50, 53–61, 378/70–90

(56) References Cited

U.S. PATENT DOCUMENTS

| | | | |
|---|---|---|---|
| 3,995,164 A | 11/1976 | Ramsay et al. | 250/510 |
| 4,671,661 A | 6/1987 | Ott | 356/402 |
| 5,386,287 A | 1/1995 | Berssen et al. | 356/326 |
| 6,249,567 B1 * | 6/2001 | Rothschild et al. | 378/63 |

FOREIGN PATENT DOCUMENTS

| | | | |
|---|---|---|---|
| EP | 295 349 A2 | 12/1988 | |
| GB | 2 309 078 A | 7/1997 | |
| WO | WO 98/51161 A1 | 11/1998 | |

* cited by examiner

*Primary Examiner*—Craig E. Church
(74) *Attorney, Agent, or Firm*—Lahive & Cockfield, LLP

(57) ABSTRACT

An apparatus comprises a source of penetrating radiation, a detector for that radiation, a sample container, and a stage between the source and the detector for supporting the sample container, wherein the sample container includes a data storage element and the apparatus includes a reader for that data storage element, the reader being connected to a control means adapted to control the apparatus on the basis of the content of the data storage element. Thus, by including information in the data storage element relating to the nature of the sample, the apparatus can be tuned to that type or class of sample and more reliable results obtained. A suitable data storage element is a bar code, and a suitable sample container is a tray. The apparatus preferably includes an image storage means for storing the output of the detector, wherein the data storage includes an identification code for a sample in the container, the image storage means being adapted to store the detector output in association with the identification code. This apparatus is particularly useful in scanning meat for bones. Containers in which the apparatus detects a bone are then presented for checking, and the stored detector output can be displayed to assist the operator. It is preferred that the stored detector output is displayed and the location of the bone in the container is identified.

49 Claims, 3 Drawing Sheets

ANALYSIS OF SAMPLES

FIELD OF THE INVENTION

The present invention relates to the analysis of sample, in particular the detection of bones in meat.

BACKGROUND ART

In the production of meat the occurrence of bones is a particular concern. This concern is greatest in processed meat where the consumer expects that all the bones have been removed and the final product is fit for safe human consumption. Chicken processing is especially concerned with bone contamination. The bones in chicken meat are softer than those in beef or pork and often can be left undetected in the final product. The processes applied to the detection of bones in meat can equally be applied to like sample analysis problems.

At present the only reliable technique for the automatic detection of bones in meat is that using x-ray technology, although other wavelengths of electromagnetic radiation have been tried. Accordingly, the description of this invention will be made in the context of x-ray scanning. However, it is applicable to other scanning methods.

An example of a typical x-ray system for the on-line detection of bones in meat is shown in FIG. 1. In this system the meat (10) passes along a conveyor belt (12) and underneath the output from an x-ray tube (14). Underneath the conveyor belt (12) is an x-ray sensor (16) which is typically a linear series of photodiodes transverse to the direction of the conveyor belt (12) which are covered with a scintillating material to convert the x-rays to light. As the meat (10) passes along the conveyor (12) the photodiodes are read out on a line by line basis thus building up a two dimensional image. The width of the image is fixed by the number of photodiode elements and the height of the image variable. The processing of the signal coming back from the photodiodes can be achieved on a line by line basis but more sophisticated processing can be achieved by building up the lines into a two dimensional frame.

Once a frame of data has been acquired signal processing techniques can be applied to the frame in order to determine the presence of a contaminant such as a bone. The simplest technique is to apply a greyscale threshold across the whole of the image obtained and to make the decision as to whether the image contains a bone/contaminant or not on the basis of whether a predetermined threshold is exceeded. Such a technique works well for products which are perfectly homogeneous and for which the likely contaminant absorbs x-rays much greater than the surrounding food medium. Such techniques are not robust for products which are not homogenous or for which the x-ray absorbtion of the defect is very close to that of the background food product. Techniques to overcome this difficulty rely on forming the meat product into a homogenous block or by floating the product in water in order to try to normalise out the meat thickness variations. Such techniques are not widely used because of hygiene and other practical meat handling considerations.

In order to overcome the limitations of simple global thresholding a number of two dimensional image processing algorithms have been developed for the detection of contaminants in x-ray images. Such techniques are dynamic entropic thresholding, morphological detection algorithms, neural network based algorithms and texture based techniques. These methods are all based on the fact that the defect (bone or other contaminant) will absorb more x-rays than the background food medium and therefore will locally appear darker in the image. These techniques are well described in the literature.

Usually such algorithms are applied to the greylevel image and result in a binary image representing those regions of the image where the defect has been segmented. In simple applications such greyscale segmentation techniques are sufficient for the isolation of any bone or other contaminants.

In many meat inspection applications such processing is not sufficient for the isolation of just the bones/contaminants since pieces of meat folded over will look just like a bone and therefore lead to a false rejection. One technique of overcoming such a difficulty is to take a number of features of the image portion which has been segmented by the greyscale segmentation algorithm. Such features could be based on the size and shape of the binary image portion and the grey level statistics of the image portion in the original grey level image. Given a large number of features obtained from bone and non bone data training sets, a pattern classification scheme could be designed to differentiate between the bone and non bone segmented image portions. Such classification schemes are commonly implemented with neural networks and in particular the Multi Layer Perceptron (MLP) network trained with a back propagation learning rule.

The system of FIG. 1 includes a neural network analysis which can automatically find bones in x-ray images of chicken meat. The image acquired from the x-ray sensor (16) is sent to a PC (18) for analysis. Morphological analysis reveals those areas where bones are likely to occur and the subsequent neural network algorithms indicate those areas which are genuine bones from those which are false rejections.

There are difficulties with such an approach. In particular, the meat varies over time due to seasonal variations, bird breed types, processing changes etc. and the x-ray sensor suffers from long term radiation damage. The present invention seeks to alleviate these.

SUMMARY OF THE INVENTION

The present invention therefore provides an apparatus comprising a source of penetrating radiation, a detector for that radiation, a sample container, and a stage between the source and the detector for supporting the sample container, wherein the sample container includes a data storage element and the apparatus includes a reader for that data storage element, the reader being connected to a control means adapted to control the apparatus on the basis of the content of the data storage element. Thus, by including information in the data storage element relating to the nature of the sample, the apparatus can be tuned to that type or class of sample and more reliable results obtained. Since the data is stored in the sample container, the process can be automated, there is no confusion as to the correct data set for a given sample and no need to time the arrival of data sets in correlation with the arrival of samples.

It will be preferred that the penetrating radiation is X-radiation but as noted above the invention is applicable to other scanning processes.

A suitable data storage element is a bar code, and a suitable sample container is a tray. These are particularly simple items to manufacture and store. The data can be encoded in the bar code, for example as a digital code. The tray is preferably open topped to allow easy access for filling and inspection.

A parameter of the apparatus that can be controlled is the source power. Some samples require a higher power in order to resolve internal detail, whereas other samples may be typically thinner and hence require lower power. This aspect of the invention therefore allows greater accuracy by avoiding the need to select a compromise power level.

The apparatus preferably includes an image storage means for storing the output of the detector, wherein the data storage includes an identification code for a sample in the container, the image storage means being adapted to store the detector output in association with the identification code. This enables a number of useful processes as will be explained.

Where the detector is a solid state device whose output can be obtained in real time, an analysis means for analysing the detector output can be incorporated in order to determine the content of the sample. A suitable analysis means for this type of work is a neural network. This can be trained to the specific type of work, and a plurality of analysis means could be provided, each for use in relation to a particular class of samples. In most cases, the analysis means will be in the form of software and a plurality thereof can most easily be provided by storing at least two sets of parameters for use in relation to the software. Thus, an analysis means can be selected by the control means according to the content of the data storage means, enabling still further or alternative improvements in accuracy.

In general, at least part of the samples will be presented for checking in association with the stored detector output. These will usually be the samples where the apparatus has detected an error or fault. There will preferably be a feedback means for training the neural network after inspection of that sample by an operator. Preferably, a location feedback device such as a touch screen monitor is provided. This enables the inspection staff to indicate the location of an error that has been missed by the system. Image features of the error can then be generated and fed back to the neural network training program. This enables more accurate training since the algorithm does not have to guess where the error is located.

The apparatus set out above is particularly useful in scanning meat for bones. Containers in which the apparatus detects a bone are then presented for checking, and the stored detector output can be displayed to assist the operator. It is preferred that the stored detector output is displayed and the location of the bone in the container is identified.

In the use of this apparatus to scan deboned meat, the plurality of analysis means when provided will most usefully be adapted to detect bones in meat originating from different areas of a carcass, such as chicken breast, chicken wing, and chicken leg. These different areas have different weights, thicknesses, absorptions etc and the ability to set a different power level and apply a different program is highly advantageous in improving accuracy.

BRIEF DESCRIPTION OF THE DRAWINGS

An embodiment of a system according to the present invention will now be described by way example with reference to the accompanying figures, in which.

DETAILED DESCRIPTION OF THE EMBODIMENTS

Figure 1:
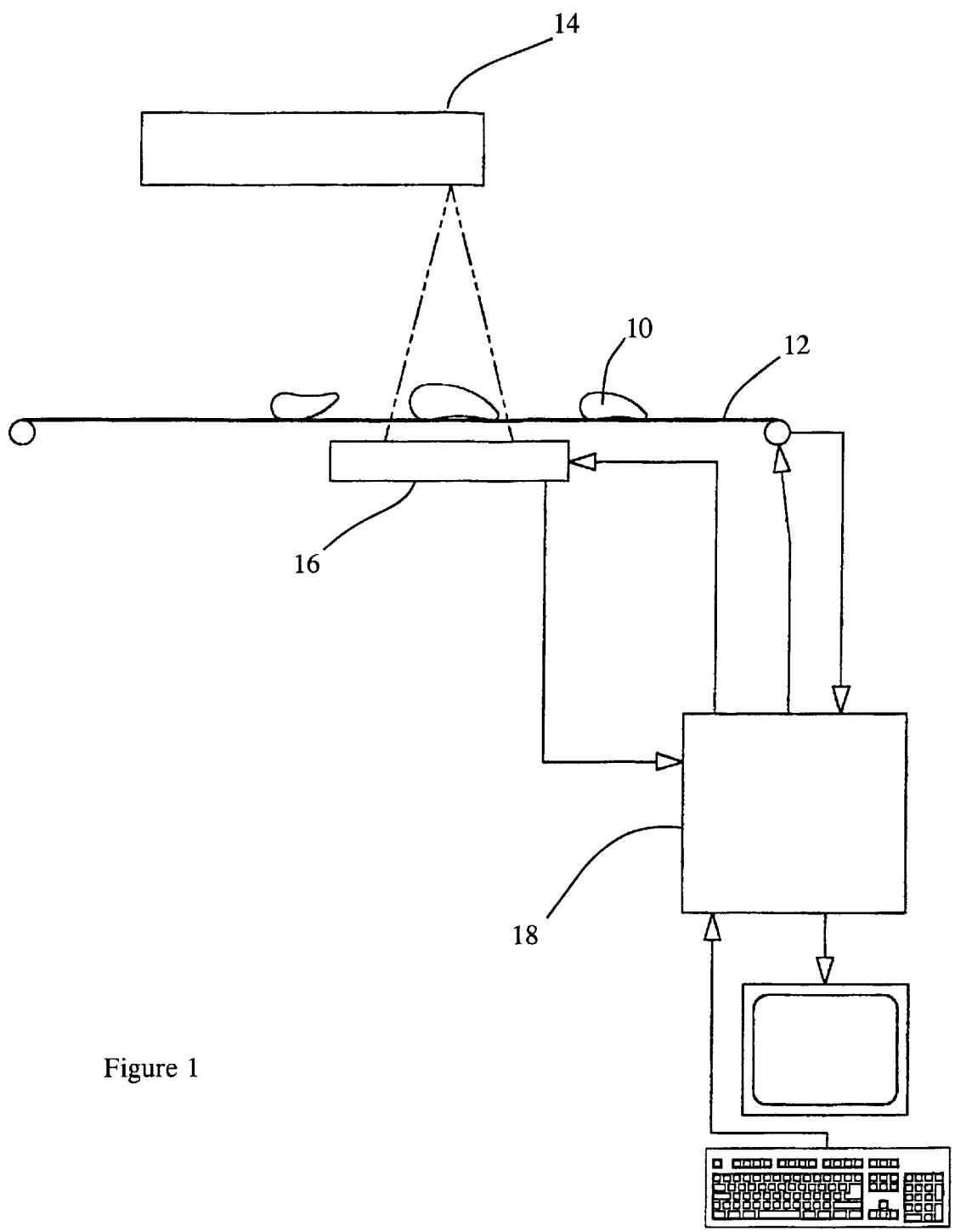
FIG. 1 already described, shows a known detection system.
Figure 2:
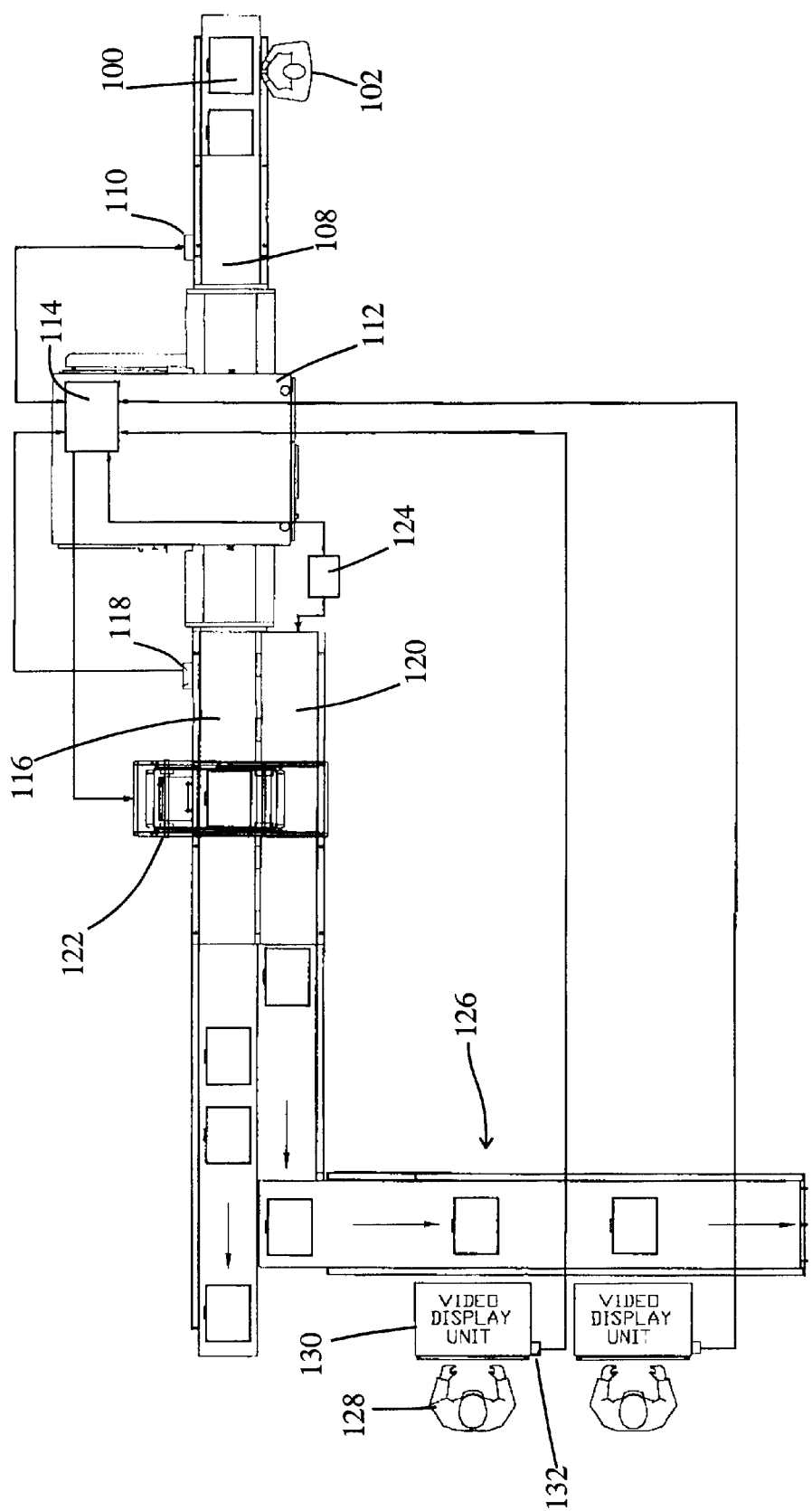
FIG. 2 shows a detection system according to the present invention.
Figure 3:
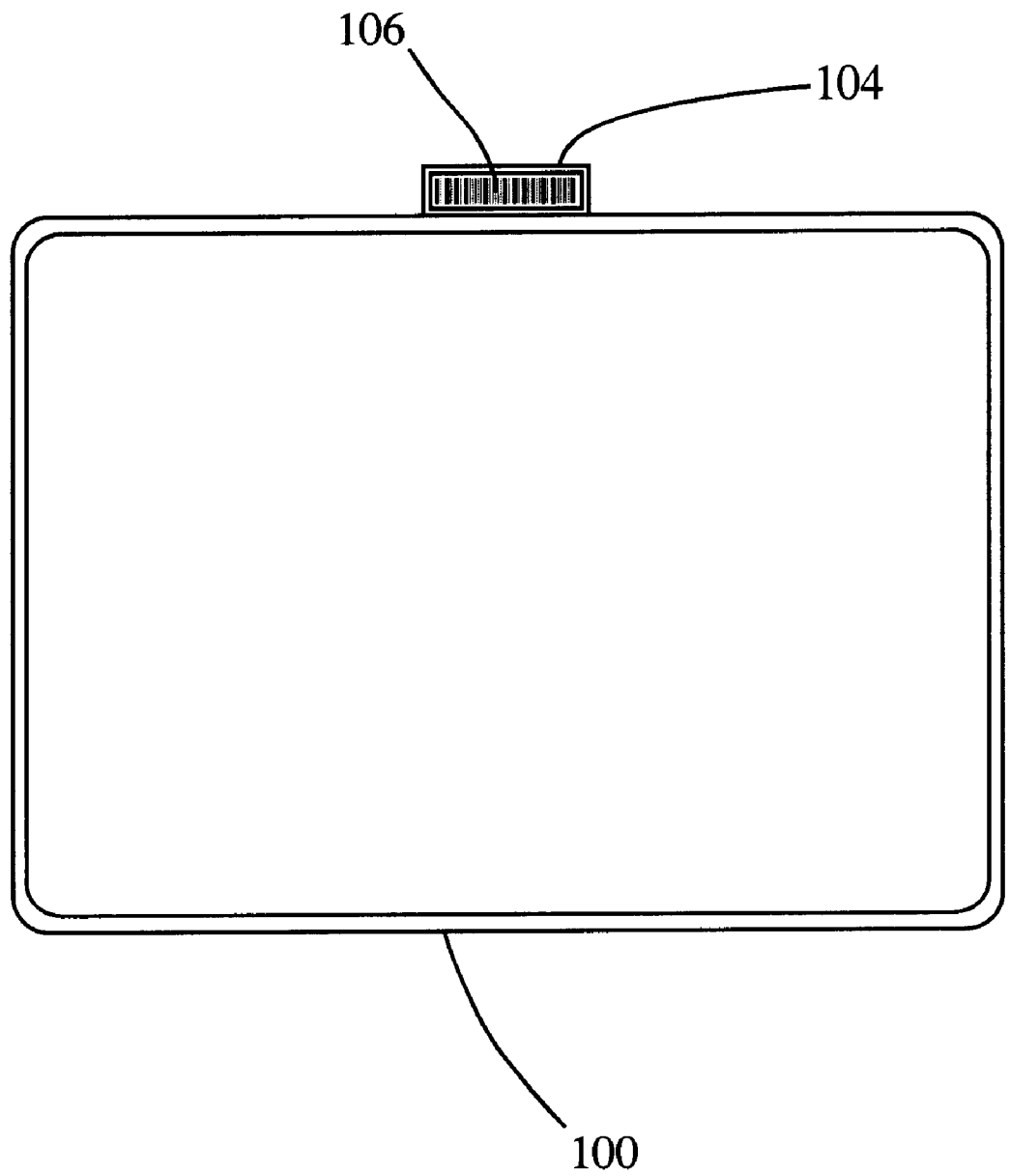
FIG. 3 shows a tray according to the present invention.

The meat to be inspected is placed in a plastic tray (100) by a human operator (102). The plastic tray (100) has a pocket (104) in which a plastic card (106) with a printed bar code is added as shown in FIG. 3. The bar code contains encoded information including an identity code for the tray, the type of bird (hen or broiler), the type of meat (leg, breast, wing, mixed) and the operator who carried out the meat de-boning and inspection process. Additional information could also be added if desired.

The tray (100) is then placed on a conveyor belt (108) along which it passes until it reaches a bar code reader (110) at the entrance to the x-ray machine (112). As the tray (100) passes by the bar code reader (110) the bar code (106) is read in and passed to a main computer (114) inside the x-ray machine. The computer then adjusts the settings of the x-ray power supply so that when the tray (100) passes under the x-ray beam the x-ray power settings are optimum for the particular tray under inspection. The reason for this is that different meats will have different thicknesses and the optimum x-ray setting for breast chicken meat is different for wing chicken meat etc. This information is obtained from the bar code.

In addition to changing the x-ray power setting the computer also changes to a preferred image processing and neural network program on the basis of the bar code read in for the specific item to be inspected. This is advantageous since it enables separate programs to learn in relation to a specific type of meat. Accordingly, these programs become tuned to detect bones in that meat type instead of becoming generalists in relation to (for example) generic chicken meat.

After the tray (100) has passed under the x-ray inspection region (112) the image will be read into the computer memory and the specific program for that type of meat will be run. The output result for that particular image will then stored and associated with the tray identity encoded in the bar code.

The tray (100) of meat will then pass onto an outfeed conveyor (116) and will pass by another bar code reader (118). When this bar code is read in the result for that particular tray will cause the tray to be deflected to a second conveyor or (120) by a deflection unit (122) if the tray of meat contains a defect (bone) or to continue undetected if the tray of meat does not contain a defect (bone). Timing and control for the pneumatic deflection unit (123) is carried out via a PLC control unit (124). Trays which do not contain a defect (bone) will therefore pass onto the next stage of production.

Trays which contain a defect (bone) are deflected onto a second conveyor (120) which then transports them to a workstation unit (126).

At the workstation unit a human inspector (128) places the tray into a holder containing a further bar code reader. As the tray is placed in the holder the bar code is read and the image stored on the computer memory is displayed on a computer display screen (130) and the area where the algorithm identified a bone is highlighted. At the point the human inspector (128) examines the tray and presses a yes/no button (132) depending on whether the tray actually contained a bone in the highlighted position. The computer program then records this feedback information to produce statistical information on the amount of bones in the different types of meat and to enable identification of those de-boners and checkers that left the bones in the meat.

The feedback information from the human checker at the workstation is also used to update the neural networks training samples used in the image processing feature classification algorithm. Initially when the inspection system is installed the system is pre- programmed with neural network data derived from historical data sets. Although this gives good starting results the systems cannot be fine tuned with data from the specific inspection application. Usually data is obtained by spending considerable time in the installation of the system at a particular customer installation. This data is then added to the preprogrammed neural network data. This has the disadvantage that it requires considerable time to be spent during the installation stage and also it does not respond to changes over time caused by product or system changes.

In addition, any trays in which bones are subsequently detected by other means can be brought to a workstation unit (126). The bar code is read and the image of that tray retrieved. The workstation includes a touch-sensitive screen on which the image is displayed, enabling the human inspector (128) to indicate where in the tray a bone was located. This enables an image processing algorithm to generate image features of the bone for supply to the neural network training program. In the absence of this, it is difficult for the software algorithm to know precisely which features correspond to the missed bone.

The invention therefore allows for a neural network architecture whose neural weight values are constantly being re-trained by feedback which occurs constantly during the operation of the inspection system. Such an adaptive training algorithm means that the neural network algorithm will be able to adapt to changes in the meat over a long period of time—such as the meat being thicker, thinner, different texture, different method of presentation on the tray, different breed of bird, different diet of bird prior to slaughter, different method of processing bird at the slaughterhouse, radiation damage of the x-ray sensor etc. Such an adaptive learning algorithm also means that the neural network can be applied to applications with little or no previous training since the training now occurs on-line rather than off-line. In addition, the separate programs for different meat types can become more accurate than a generic program for all meat types.

It will of course be understood that the above example is purely illustrative of the present invention, and that many variations may be made thereto without departing from the scope of the invention.

What is claimed is:

1. Apparatus comprising
   a source of penetrating radiation and a detector for that radiation,
   a sample container,
   a stage between the source and the detector arranged to support the sample container, wherein the sample container includes a data storage element and the apparatus includes a reader for that data storage element, the reader being connected to a control means adapted to control the apparatus on the basis of the content of the data storage element, the data storage including an identification code for a sample in the container, and
   an image storage means for storing the output of the detector in the form of an image, the image storage means being adapted to store the detector output in association with the identification code.

2. Apparatus according to claim 1 in which the penetrating radiation is X-radiation.

3. Apparatus according to claim 1 in which the data storage element is a bar code.

4. Apparatus according to claim 1 in which the sample container is a tray.

5. Apparatus according to claim 4 in which the tray is open topped.

6. Apparatus according to claim 1 for use in scanning meat for bones, including means for presenting containers in which the apparatus detects a bone for checking in association with the stored detector output.

7. Apparatus according to claim 6 including means for displaying the stored detector output, said means being arranged to identify the location of the bone in the container.

8. Apparatus according to claim 1 including analysis means for analysing the detector output to determine the content of the sample.

9. Apparatus according to claim 8 in which the analysis means includes a neural network.

10. Apparatus according to claim 8 in which a plurality of analysis means are provided, each for use in relation to a class of samples.

11. Apparatus according to claim 10 in which the analysis means are in the form of software and the plurality thereof comprises at least two sets of parameters for use in relation to the software.

12. Apparatus according to claim 10 in which an analysis means is selected by the control means according to the content of the data storage means.

13. Apparatus according to claim 9 including means for sorting the samples according to the result of the neural network analysis.

14. Apparatus according to claim 13 including means for presenting at least part of the samples for checking in association with the stored detector output.

15. Apparatus according to claim 14 including a feedback means for training the neural network.

16. Apparatus according to claim 10 for use in scanning meat for bones, in which the plurality of analysis means are adapted to detect bones in meat originating from different areas of a carcass.

17. Apparatus according to claim 16 in which the analysis means are adapted to detect bones in one of chicken breast, chicken wing, and chicken leg.

18. Apparatus for use in scanning meat for bones comprising
   a source of penetrating radiation,
   a detector for that radiation,
   a sample container, and
   a stage between the source and the detector arranged to support the sample container, wherein the sample container includes a data storage element and the apparatus includes a reader for that data storage element, the reader being connected to a control means adapted to control the apparatus on the basis of the content of the data storage element.

19. Apparatus according to claim 18 in which the penetrating radiation is X radiation.

20. Apparatus according to claim 18 in which the data storage element is a bar code.

21. Apparatus according to claim 18 in which the sample container is a tray.

22. Apparatus according to claim 21 in which the tray is open topped.

23. Apparatus according to claim 18 in which the control means is adapted to control the source power.

24. Apparatus according to claim 18 including analysis means for analysing the detector output to determine the content of the sample.

25. Apparatus according to claim 24 in which the analysis means includes a neural network.

26. Apparatus according to claim 25 including means for sorting the samples according to the result of the neural network analysis.

27. Apparatus according to claim 26 including means for presenting at least part of the samples for checking in association with the stored detector output.

28. Apparatus according to claim 27 including a feedback means for training the neural network.

29. Apparatus according to claim 24 in which a plurality of analysis means are provided, each for use in relation to a class of samples.

30. Apparatus according to claim 29 in which the analysis means are in the form of software and the plurality thereof comprises at least two sets of parameters for use in relation to the software.

31. Apparatus according to claim 29 in which an analysis means is selected by the control means according to the content of the data storage means.

32. Apparatus comprising
a source of penetrating radiation,
a detector for that radiation,
a sample container, and
a stage between the source and the detector arranged to support the sample container, wherein the sample container includes a data storage element, the apparatus includes a reader for that data storage element, the reader being connected to a control means adapted to control the source power of the apparatus on the basis of the content of the data storage element.

33. Apparatus according to claim 32 for use in scanning meat for bones, including means for presenting containers in which the apparatus detects a bone for checking in association with the stored detector output.

34. Apparatus according to claim 33 including means for displaying the stored detector output, said means being arranged to identify the location of the bone in the container.

35. Apparatus according to claim 32 including analysis means for analysing the detector output to determine the content of the sample.

36. Apparatus according to claim 32 in which the penetrating radiation is X-radiation.

37. Apparatus according to claim 32 in which the data storage element is a bar code.

38. Apparatus according to claim 32 in which the sample container is a tray.

39. Apparatus according to claim 38 in which the tray is open topped.

40. Apparatus according to claim 32 including an image storage means for storing the output of the detector, wherein the data storage includes an identification code for a sample in the container, the image storage means being adapted to store the detector output in association with the identification code.

41. Apparatus according to claim 35 in which a plurality of analysis means are provided, each for use in relation to a class of samples.

42. Apparatus according to claim 35 in which the analysis means includes a neural network.

43. Apparatus according to claim 42 including means for sorting the samples according to the result of the neural network analysis.

44. Apparatus according to claim 41 in which the analysis means are in the form of software and the plurality thereof comprises at least two sets of parameters for use in relation to the software.

45. Apparatus according to claim 41 in which an analysis means is selected by the control means according to the content of the data storage means.

46. Apparatus according to claim 41 for use in scanning meat for bones, in which the plurality of analysis means are adapted to detect bones in meat originating from different areas of a carcass.

47. Apparatus according to claim 43 including means for presenting at least part of the samples for checking in association with the stored detector output.

48. Apparatus according to claim 47 including a feedback means for training the neural network.

49. Apparatus according to claim 46 in which the analysis means are adapted to detect bones in one of chicken breast, chicken wing, and chicken leg.

* * * * *